United States Patent
Buzot

(10) Patent No.: US 6,673,032 B2
(45) Date of Patent: Jan. 6, 2004

(54) APPLICATOR HAVING IMPROVED GRIPPER END

(75) Inventor: Herve Buzot, North Brunswick, NJ (US)

(73) Assignee: McNeil-PPC, Inc., Skillman, NJ (US)

( * ) Notice: Subject to any disclaimer, the term of this patent is extended or adjusted under 35 U.S.C. 154(b) by 0 days.

(21) Appl. No.: 09/823,145

(22) Filed: Mar. 30, 2001

(65) Prior Publication Data

US 2002/0143287 A1 Oct. 3, 2002

(51) Int. Cl.$^7$ ................................................. A61F 13/20

(52) U.S. Cl. ....................................... 604/15; 264/328.2

(58) Field of Search ...................... 609/11–18, 285–288, 609/311, 57–60; 264/239, 328.1, 328.2

(56) References Cited

U.S. PATENT DOCUMENTS

| | | |
|---|---|---|
| 2,330,257 A | 9/1943 | Bailey |
| 3,042,040 A | * 7/1962 | Galik ........................... 604/15 |
| 3,297,031 A | * 1/1967 | Bray ........................... 604/59 |
| 3,347,234 A | 10/1967 | Voss |
| 3,433,225 A | 3/1969 | Voss et al. |
| 3,572,339 A | 3/1971 | Voss et al. |
| 3,575,169 A | * 4/1971 | Voss ........................... 604/15 |
| 3,717,149 A | 2/1973 | Morane |
| 4,048,998 A | 9/1977 | Nigro |
| D250,663 S | 12/1978 | Koch et al. |
| 4,198,978 A | 4/1980 | Nigro |
| 4,329,991 A | 5/1982 | Sakurai |
| 4,361,150 A | 11/1982 | Voss |
| 4,447,222 A | 5/1984 | Sartinoranont |
| 4,508,531 A | 4/1985 | Whitehead |
| 4,573,963 A | 3/1986 | Sheldon |
| 4,573,964 A | 3/1986 | Huffman |
| 4,620,534 A | 11/1986 | Zartman |
| 4,755,164 A | 7/1988 | Hinzmann |
| 4,900,299 A | 2/1990 | Webb |
| 4,921,474 A | 5/1990 | Suzuki et al. |
| 4,923,440 A | 5/1990 | Genaro |
| 5,002,526 A | 3/1991 | Herring |
| 5,041,080 A | 8/1991 | Shimatani et al. |

(List continued on next page.)

FOREIGN PATENT DOCUMENTS

| | | |
|---|---|---|
| DE | 1 948 979 | 4/1971 |
| EP | 0 291 343 | 11/1988 |
| EP | 0481484 B1 | 4/1992 |
| GB | 1108291 | 4/1968 |
| GB | 1272863 | 5/1972 |
| GB | 1272864 | 5/1972 |
| GB | 2166656 | 5/1986 |
| GB | 2 166 656 A | 5/1986 |
| WO | WO01/00125 A1 | 1/2001 |
| ZA | 7208833 | 9/1973 |

OTHER PUBLICATIONS

PCT International Search Report, PCT/US02/09302, Jul. 16, 2002.
U.S. patent application Ser. No. 09/602,950 (PPC–732).
U.S. patent application Ser. No. 09/454,989 (J&J 1733).

Primary Examiner—Dennis Ruhl

(57) ABSTRACT

The present invention relates to a gripping member for use on a tubular insertion member of an applicator for inserting an object into a body cavity. The gripping member includes a plastic sleeve having a longitudinal axis, first and second ends, an outer surface, and a bore extending from the first end to the second end. It also includes a plurality of raised features disposed on the outer surface of the body, extending away from the longitudinal axis. At least one of the raised features is proximate the first end, and at least one of the raised features is proximate the second end. Finally, at least one notch defined by side edges is disposed at one of the first and second ends to impart flexibility to the associated end. The plastic sleeve is arranged and configured to be affixed to the associated tubular insertion member.

19 Claims, 6 Drawing Sheets

U.S. PATENT DOCUMENTS

| | | |
|---|---|---|
| 5,080,659 A | 1/1992 | Nakanishi |
| 5,158,535 A | 10/1992 | Paul et al. |
| 5,330,421 A | 7/1994 | Tarr et al. |
| 5,346,468 A | 9/1994 | Campion et al. |
| 5,350,354 A | 9/1994 | Billmers |
| 5,350,371 A | 9/1994 | Van Iten |
| 5,554,108 A | 9/1996 | Browning et al. |
| 5,702,553 A | 12/1997 | Iskra et al. |
| 5,709,652 A | 1/1998 | Hagerty |
| 5,782,793 A | 7/1998 | Nielsen et al. |
| 5,782,794 A | 7/1998 | Assenheimer Downs |
| 5,788,663 A | 8/1998 | Igaue et al. |
| 5,788,664 A | 8/1998 | Scalise |
| 5,827,214 A | 10/1998 | Fox et al. |
| 5,910,520 A | 6/1999 | Dabi et al. |
| D415,565 S | 10/1999 | Hayes et al. |
| 6,171,426 B1 | 1/2001 | Blanchard |

\* cited by examiner

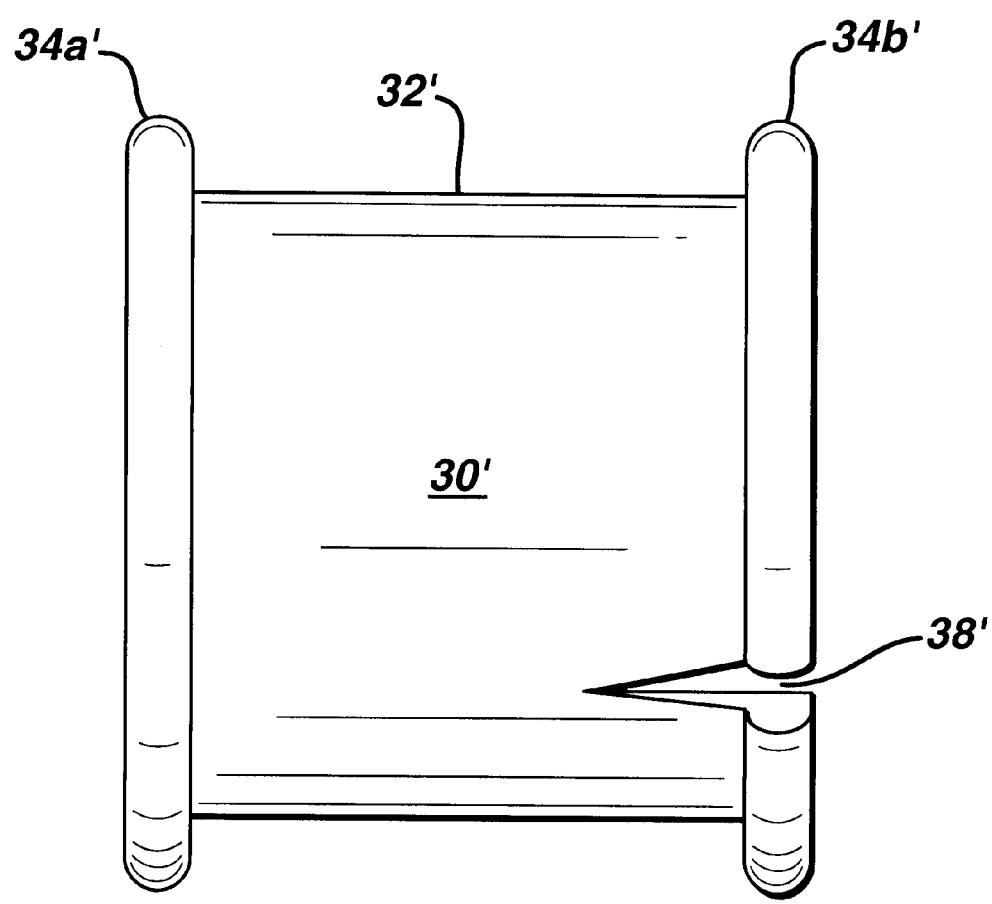

APPLICATOR HAVING IMPROVED GRIPPER END

CROSS-REFERENCE TO RELATED APPLICATIONS

This invention is related to the following copending application: U.S. Ser. No. 09/602,950, filed Jun. 23, 2000, entitled "Applicator For Catamenial Device Having Improved Gripper End".

FIELD OF THE INVENTION

The present invention provides an applicator comprising a tubular insertion member and a retrofitted gripping member. The applicator is particularly useful for delivering a catamenial device into the vaginal canal, such as a tampon or menstrual collection cup.

BACKGROUND OF THE INVENTION

Applicators for inserting and expelling objects into a body cavity typically comprise a tubular insertion member having an insertion end and a gripper end opposite thereof, and an expulsion member slideable within the tubular insertion member. The gripper end generally incorporates features to allow a user to more or less securely hold the applicator during use—inserting the applicator into a body cavity, expelling a substantially enclosed object contained by the applicator, and withdrawing the applicator from the body. Unfortunately, many applicators known in the art comprise a gripping section that exhibits a weakness during at least one of the three above-identified steps of using the applicator.

Voss, U.S. Pat. No. 4,361,150, and Sartinoranont, U.S. Pat. No. 4,447,222, incorporates projections, such as a ring, at the trailing end of the applicator member. These projections provide resistance to rearward finger slippage during the expulsion step of using an applicator, and they may help the user to remove the applicator from her body.

Whitehead, U.S. Pat. No. 4,508,531, reduces the diameter of the applicator in the vicinity of the tubular insertion member trailing end. The reduced diameter creates a shoulder near the insertion end to resist finger slippage toward the insertion end during the insertion step.

Both of these approaches suffer from providing resistance to finger slippage in only one direction. Efforts to provide resistance in two directions, as disclosed in the art, suffer from shortcomings as well.

First, Voss, U.S. Pat. No. 3,575,169, increases the friction on the trailing end of the tubular insertion member by coating it with pulverized stone or sand. This may be especially helpful as applicator manufacturers are moving toward the use of higher gloss surfaces, which are purported to aid in ease of applicator insertion into a body cavity.

Second, Hagerty, U.S. Pat. No. 5,709,652, employs a plurality of finger-accepting apertures in the applicator to provide relatively abrupt, finger-accepting edges. These edges frictionally resist movement of a user's finger in response to longitudinal forces on the device. Although a useful contribution to the art, the finger-accepting edges disclosed by Hagerty, are generally limited to the wall thickness of the applicator.

Finally, Suzuki et al., U.S. Pat. No. 4,921,474, discloses a sanitary tampon applicator comprising a plastic outer sleeve having a diameter-reduced section along a length adjacent its rear end so as to form an annular shoulder, and a annular rib at its rear open end. This device has two or more physical restraints as a means for the user to hold the applicator securely during all of the steps of use. It is noteworthy that the Suzuki applicator is limited to a "plastic" outer sleeve. One skilled in the art would recognize that it would be difficult to form similar physical restraints (shoulder and rib) on a paperboard applicator. Plastic applicators incorporating such design features traditionally employ sophisticated molds and processes in injection molding operations, e.g., comprising split cores and/or side slides. The resulting mold designs and processing steps can add significant costs to the final product.

Accordingly, what is needed, is an applicator that can be manufactured by low-cost, high-speed equipment and ejected by operation of an injection molding device in a single direction and retrofitted with a superior gripping member that has features to help during insertion of the applicator into a body cavity, expulsion of a contained object, and withdrawal of the applicator from the body.

SUMMARY OF THE INVENTION

The present invention relates to a gripping member for use on a tubular insertion member of an applicator for inserting an object into a body cavity. The gripping member includes a plastic sleeve having a longitudinal axis, first and second ends, an outer surface, and a bore extending from the first end to the second end. It also includes a plurality of raised features disposed on the outer surface of the body, extending away from the longitudinal axis. At least one of the raised features is proximate the first end, and at least one of the raised features is proximate the second end. Finally, at least one notch defined by side edges is disposed at one of the first and second ends to impart flexibility to the associated end. The plastic sleeve is arranged and configured to be affixed to the associated tubular insertion member.

The invention also relates to a method for forming a gripping member for use on a tubular insertion member of an applicator for inserting an object into a body cavity. The method includes forming a substantially tubular mold cavity between a first mold plate and a second mold plate; injecting molten plastic material into the mold cavity; cooling the plastic material in the mold cavity to form the gripping member; opening the mold and ejecting the gripping member. The mold cavity has features of increased thickness at a first end and at a second end and at least one notch-forming insert disposed at one of the first and second ends. The gripping member has a first end and a second end corresponding to the first and second ends of the mold cavity and at least one flex-enhancing notch corresponding to the at least one notch-forming insert in the mold cavity. The at least one notch allows the end associated therewith to flex sufficiently to permit separating the mold plates and stripping the gripping member.

BRIEF DESCRIPTION OF THE DRAWINGS

FIG. 7 is a side view of an alternative gripping member having two distally located flanges separated by a cylindrical portion.

DETAILED DESCRIPTION OF THE INVENTION

Figure 1:
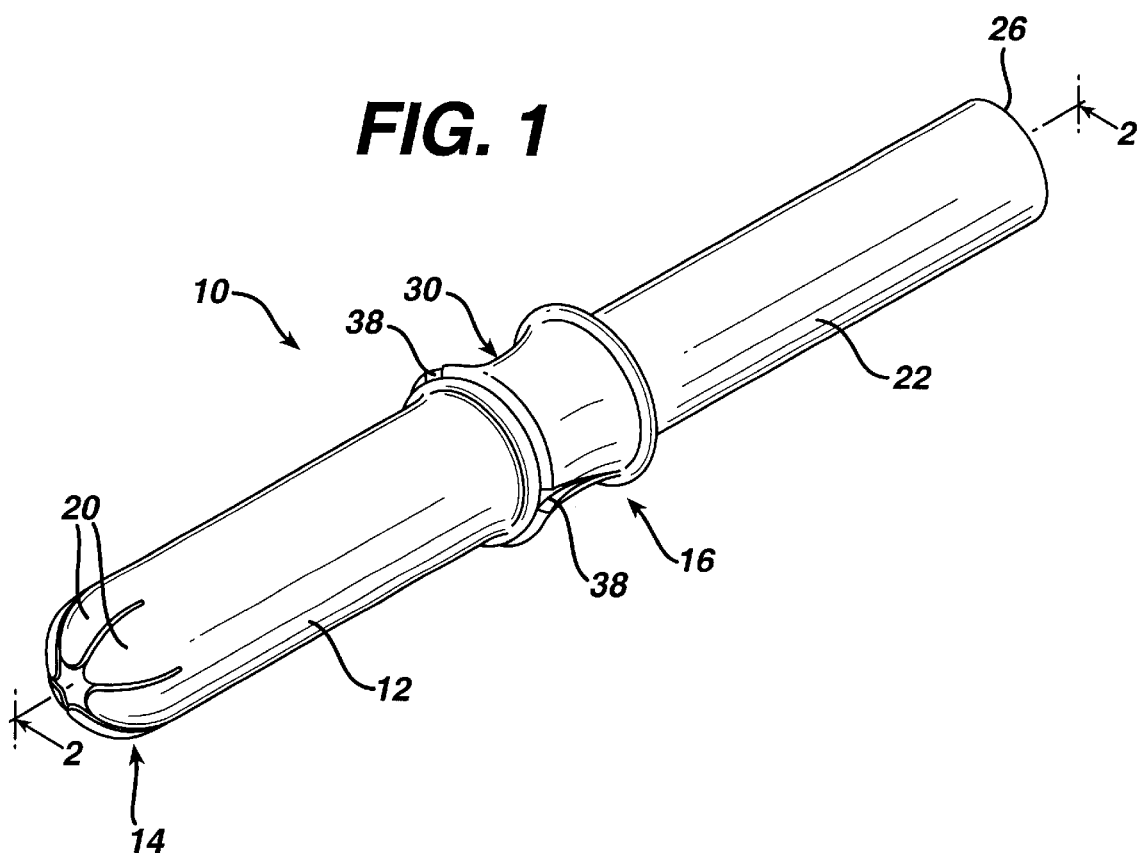
FIG. 1 is a perspective view of an applicator according to the present invention having a novel gripping member retrofitted onto the trailing end of a tubular insertion member.

As used herein in the specification and claims, the term "perimeter" relates to the measurement about the structure as measured in and defined by a plane perpendicular to the longitudinal axis of the blank or the insertion member. This measurement may be on the inside or the outside of the structure. The perimeter of a substantially tubular structure is related to its diameter.

As used herein in the specification and claims, the term "diameter" means a chord passing through the center of a figure or body; the length of a straight line through the center of an object.

As used herein the specification and the claims, the phrase "coincident diameter" (and variants thereof) relates to diameters of two or more elements extending through the same point and along the same line or plane.

As used herein, a "unitary" device is one that has the characteristic of being a unit or a whole. This includes both devices that are created from a single element and those formed by fixing together individual elements to form the whole.

As used herein the specification and the claims, the term "intravaginal device" and related terms includes support devices, obstructing devices useful to block the flow of and/or collect bodily liquids, and the like. The term includes, without limitation, incontinence devices and vaginal supports, such as pessaries; and obstructing devices, such as menstrual collection cups and inflatable or expandable vaginal blocking devices (devices which do not, themselves, absorb the bodily liquids).

As used herein the specification and the claims, the term "rigidity" and related terms mean the longitudinal stability of the device. Normally specified as the unit for rigidity is the force that is necessary to compress the element in the longitudinal direction by a specific length (N/cm).

As used herein the specification and the claims, the term "raised feature" and related terms mean an individual element or series of elements working together as an identifiable group that extend above a level of the adjoining surface. Examples of raised features include, without limitation, a continuous ring, an intermittent ring, a line, bumps, embossments, and the like.

While the present invention generally relates to applicator devices having a tubular insertion member for delivering materials into body cavities, the following detailed description will refer, specifically, to a tampon applicator for ease of understanding. One of ordinary skill in the art will recognize other uses for this invention.

More particularly, the present invention provides an applicator comprising a tubular insertion member and a retrofitted, superior gripping member, employing design features that aid in inserting the applicator into a body cavity, expelling a contained object, and withdrawing the applicator from the body. Manufacturing the gripping member separately provides numerous advantages, some of which will be discussed below.

One significant advantage is the versatility of materials and processes available for manufacturing the tubular insertion and expulsion members. Paperboard products appeal to both the manufacturer and the consumer, derived from factors such as ease of manufacture, cost of manufacture, purchase cost, environmental benefits, and flushability convenience. However, their features intended to aid the consumer in handling the product during use have been limited. Embossed rings and finger-accepting apertures are typically confined to the gauge of the paperboard (or combined layers) used. A superior gripping member, manufactured separately, can be retrofitted onto a paperboard tubular insertion member, without significantly eliminating any of the noted appeal.

In this manner, the gripping member itself can provide a substantial portion of the structural stability necessary for inserting and expelling objects into body cavities. Therefore, a minimum amount of paperboard or an extremely thin-walled polymeric tube may be used in conjunction with the gripping member as a complete and useful system. This approach can reduce the cost of manufacture down and eliminate the likelihood that the applicator may collapse during use.

A second advantage offered by separate component manufacturing is realized through the option of using state of the art high-speed equipment, such as disclosed in Hinzmann, U.S. Pat. No. 4,755,164, the disclosure of which is herein incorporated by reference, and commercially available from Hauni Richmond, Inc. of Richmond, Va. Hinzmann employs reservoir systems that accumulate applicator components between major steps of manipulation and assembly. Applicators with any significant projections extending from their outer surfaces will not stack neatly (parallel) in the reservoir systems, thereby reducing the efficiency of space and transfer. Such products may also create process downtime due to applicators being "hung up" in the accumulators. The reservoir systems provide efficiency in multi-component manufacturing by maintaining continuous overall production even during downtime of an upstream piece of equipment. Manufacture of the tubular insertion member, expulsion member, and e.g., tampons, as well as component assembly, can take place with the gripping member retrofitted as a final step prior to packaging.

Figure 2:
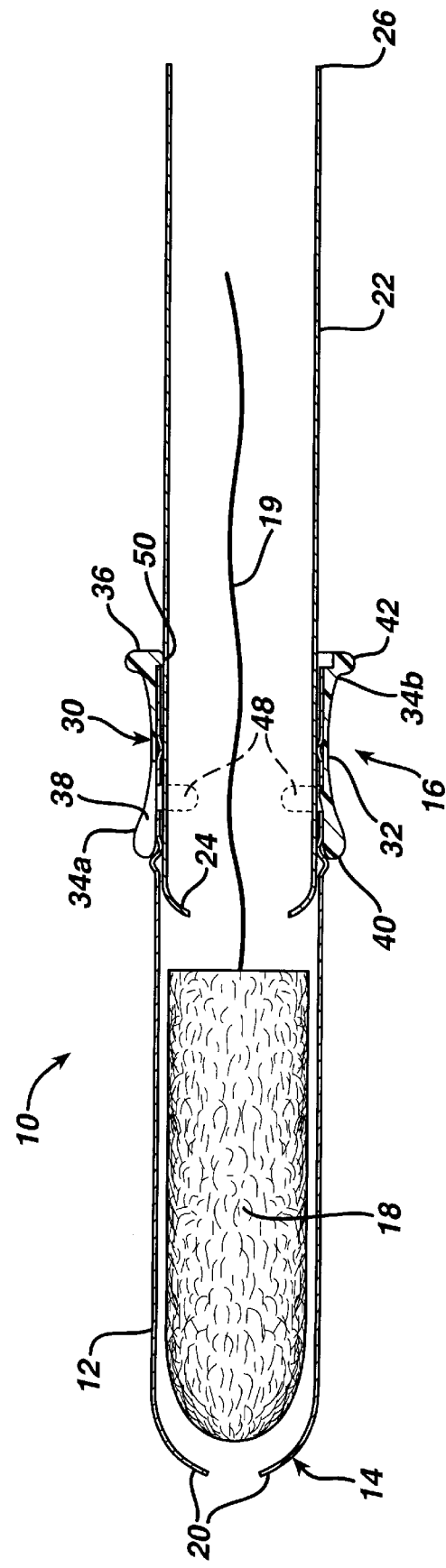
FIG. 2 is a cross-section along line 2—2 of FIG. 1.
Figure 3:
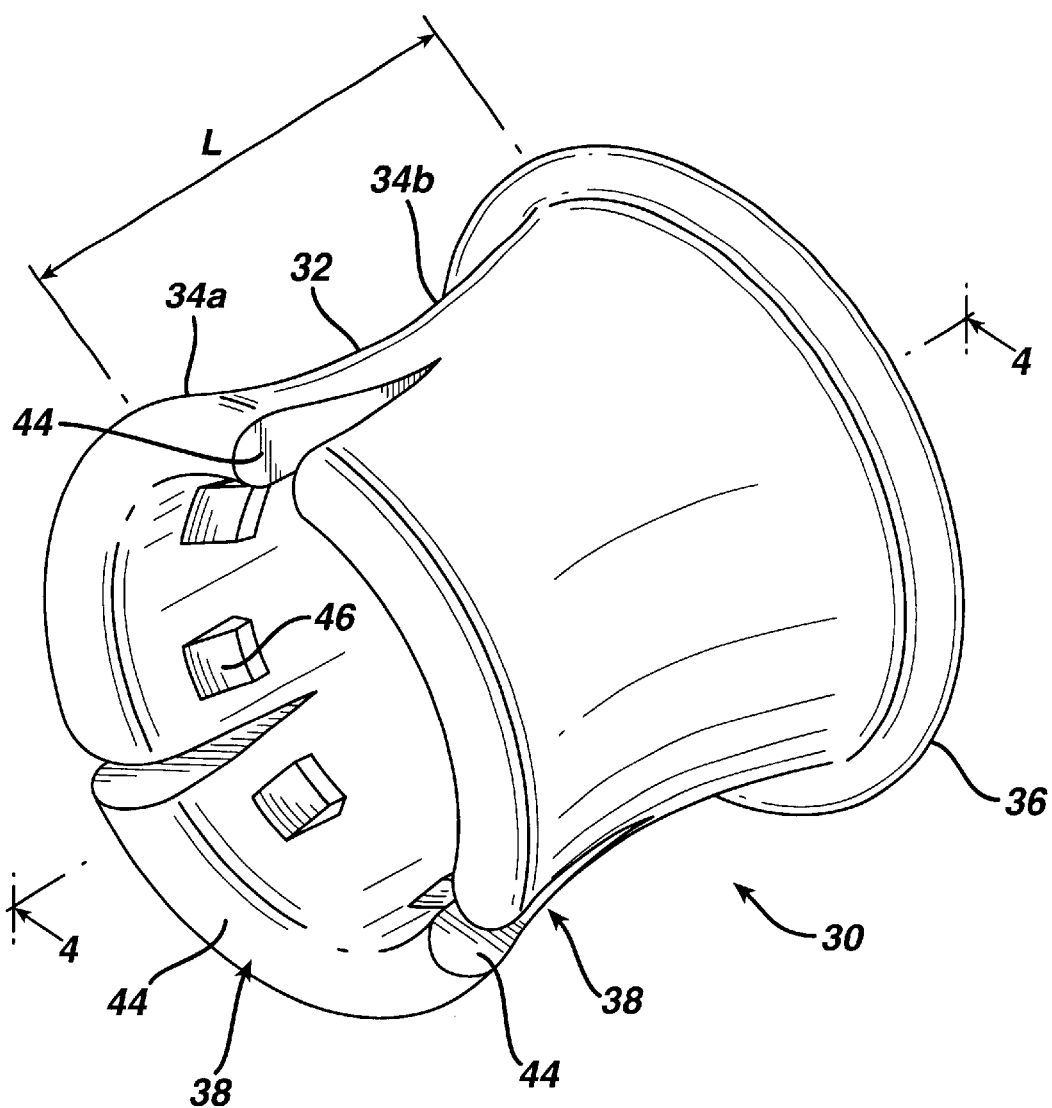
FIG. 3 is a perspective view of a preferred gripping member.

Referring now to the drawings, wherein like reference numerals designate like elements, FIGS. 1 and 2 depict an applicator 10, comprising a tubular insertion member 12, having an insertion end 14 to a gripper end 16 that is suitable to contain a tampon 18 having a withdrawal string 19 that can be delivered into the body cavity. The insertion end may have a plurality of inwardly curved petals 20 that form a substantially closed feature. The applicator 10 also includes an expulsion member 22 having a first end 24 that is insertable into the tubular insertion member 12 and is capable of bearing against the tampon 18. The expulsion member 22 terminates in a second end 26, opposite the first end 24, that may be manipulated to move the first end 24 within the tubular insertion member 12. The first end 24 of the expulsion member 22 is arranged and configured to be slideably introduced into the tubular insertion member 12 through its gripper end 16.

The applicators 10 or other tubular devices of the present invention can have tube geometries or cross-sections that are useful to contain the object to be inserted. Often, the shape of the tampon 18 contained suggests the shape of the tubular insertion member 12, but departures from this general rule may be made. Therefore, the tubular insertion member 12 may take on numerous cross-sectional shapes including, without limitation, circular, oval, polygonal (e.g., trapezoidal, rectangular, triangular), and the like. For example, cylindrical tampons may be contained within rectangular insertion members and trapezoidal tampons (such as those disclosed in Van Iten et al., U.S. Pat. No. 5,350,371) and cup-shaped tampons (such as those disclosed in Bailey, U.S. Pat. No. 2,330,257) can be contained in a generally cylindrical insertion member. In addition, the insertion member 12 can substantially elongated, curved, or flexible, or it can take on other shapes that are apparent to one of ordinary skill in the art. The specific geometry, itself, is not critical to the practice of the present invention. In addition, the edge of the tubular device (both finished and unfinished) may be a standard, planar edge coincident with a plane perpendicular to the longitudinal axis of the tubular device. However, the edge may also be coincident with a plane oblique to the longitudinal axis, or it may be otherwise contoured and/or recessed as described in the commonly assigned, copending application of Buzot, U.S. Ser. No. 09/454,989 (herein incorporated by reference).

The applicator can be made of plastic, biodegradable material or cardboard. In particular plastic such as any of the representative list including, without limitation, polyolefins such as polyethylene and polypropylene (including polyolefin copolymers); polyesters such as polyethylene terephthalate; polyamides such as nylon; polyurethanes; polystyrene; polycaprolactone; polyvinyl alcohol; ethylene-vinyl acetate copolymers; elastomers such as silicones, natural rubbers, and synthetic rubbers including block copolymers; cellophane; PHBV such as those disclosed in Dabi et al., U.S. Pat. No. 5,910,520 (herein incorporated by reference); starch-based polymers including those disclosed in Dabi et al., U.S. Pat. No. 5,910,520; and the like can be used. The expulsion member can be formed as a solid or a tubular element.

The applicator devices of the present invention can be made of materials known to those of ordinary skill in the art. Generally, the applicators may be plastic or paper. Plastic materials include, without limitation, polyolefins such as polyethylene and polypropylene, polyesters such as polyethylene terephthalate, polycaprolactone, polyvinyl alcohol, ethylene-vinyl acetate copolymers, cellophane, PHBV such as those disclosed in Dabi et al., U.S. Pat. No. 5,910,520 (herein incorporated by reference), starch-based polymers including those disclosed in Dabi et al., U.S. Pat. No. 5,910,520, and the like.

Paper materials include, without limitation, paperboard, cardboard, cup stock, paper, and the like. The paper may be a single layer of material, or it can be a plurality of laminated layers to provide multiple benefits relating to the various layers. Laminated paper material may include a surface layer or coating of plastic, wax, silicone, lubricants, and the like, which may be useful to increase the comfort to the user during insertion and withdrawal. The plastic coating may include, without limitation, those plastic materials listed above. Laminated paper material may also include additional layers such as adhesive layers, tie layers, and the like.

An example of such a surface layer is disclosed in Blanchard, U.S. Pat. No. 6,171,426. A representative, non-limiting list of useful materials to be used as the surface layer includes, waxes, cellophane, polyolefins, polyesters, epoxies, and the like. The surface layers may also include thermal stabilizers, pigments, fragrances, surfactants, anti-microbial agents, medicaments, and the like.

Typical dimensions for each of the tubular insertion and expulsion members include a length of from about 50 to about 100 millimeters, a diameter of from about 8 to about 16 millimeters, and a thickness of from about 0.4 to about 0.6 millimeters. Preferably, the diameter of the expulsion member is less than the diameter of the tubular insertion member to allow for a telescopic arrangement of the two.

The tubular insertion member of the applicator provided by the present invention is preferably substantially closed prior to expulsion of the materials contained therein. Alternatively, the insertion end of the applicator can be more or less open, that is the diameter along the length of the tubular insertion member is substantially equivalent to the diameter of the insertion end. Procter & Gamble, of Cincinnati, Ohio, currently offers for sale an open-ended tampon applicator under the trade name TAMPAX flushable applicator tampons.

The applicator 10 further comprises a gripping member 30, which is manufactured separately from the insertion and expulsion members and thereafter affixed, preferably immovably, to at least a portion of the gripper end of the tubular insertion member. The gripping member 30 includes a plastic sleeve having a longitudinal axis and a bore extending from a first end to a second end. The outer surface of the gripping member has a plurality of raised features disposed thereon, extending away from the longitudinal axis. At least one of the raised features is proximate each of the first and second ends of the gripping member. The gripping member also incorporates at least one notch defined by side edges and disposed at one of the first and second ends.

FIGS. 1–5 depict a preferred embodiment of the gripping member 30, having a minimum outer diameter "D", a length "L", and an intermediate area 32 disposed between two longitudinally separated raised areas 34a and 34b. The curvilinear transition between the intermediate area and the two raised areas preferably forms a "saddle-shaped" profile. This profile provides comfort and control by corresponding to the natural curvature of a user's manual digits (thumb and fingers). An optional flange 36 is also depicted in the figures. The flange 36 provides a structure for the user to grasp to withdraw the insertion member from a body cavity, and it can also be used to orient the gripping member 30 during assembly of the applicator 10.

The gripping member 30 also incorporates at least one notch, preferably plurality of notches 38, disposed on or about one of its first and second ends 40, 42. The notches 38 impart flexibility to the associated end of the gripping member 30. In particular, these notches 38 permit the associated end to flex, especially radially inwardly and perhaps also outwardly, during the manufacture of the gripping member 30 and during assembly of the application 10. Although the notches 38 are illustrated in FIGS. 1–5 as being located about the first end 40 of the gripping member 30, it will be recognized that these notches 38 could be located about the second end 42 of the gripping member 30, or indeed, about both ends. The number of notches 38 included in the gripping member 30 may be suggested by the characteristics of the material used to make the gripping member 30. The at least one notch 38 is useful to enhance the flexibility of the associated end. A plurality of notches 38 is desirable to distribute their flex-enhancing properties about the associated end. Preferably, there are between two and about 20, and more preferably between three and six, of these notches 38 disposed about the end of the gripping member 30.

Preferably, the length of a notch is selected to provide sufficient flexibility to the associated gripping member end. As either the outside or inside diameter of the gripping member varies, and especially if the end of the gripping member has a greater outside diameter than the intermediate area (as shown in FIG. 2), it is preferred that at least one notch extends into a portion of the gripping member having a reduced outside diameter. More preferably, the at least one notch extends until it reaches the smallest outside diameter of the sleeve (within a tolerance of about 0.3 mm, and preferably less than 0.3 mm). If more than one notch is employed, it is also preferred that substantially all notches extend to a portion of the gripping member having the minimum outside diameter. This allows the gripping member to flex sufficiently to be ejected from the confines of the mold as discussed in greater detail below. While this paragraph has discussed a variation of the outside diameter, one of ordinary skill in the art will recognize the similar constraints if the inside diameter also varies or is the only diameter that varies.

The gripping member length "L" is at least about 5 millimeters, and preferably at least about 10 millimeters. Such a length of the gripping member allows the user to grasp the gripping member, rather than placing her manual digits (e.g., fingers) on either side of it. The gripping member should be of sufficient minimum length, such that the utility of design features employed to provide resistance to movement of the user's fingers, is not compromised. The at least one notch may also extend nearly to the end of the gripping member opposite the notched end. However, the at least one notch should not so greatly weaken the gripping member to allow it to be easily split or to reduce its ability to sufficiently maintain its position on the tubular insertion member. For example, if the length of the gripping member is capable of accepting the user's manual digits, especially between longitudinally separated raised areas, it becomes less likely that the user's fingers, etc., would span the distance between these raised areas and lose the benefits of the present invention. Such a distance of the span "S" is preferably at least about 0.35 inches (about 9 mm), more preferably about 0.4 to about 0.6 inches (about 10 mm to about 15 mm). With a gripping member having these dimensions, the notches could have a length between about 3 to about 10 mm, more preferably between about 5 and about 8 mm.

Each notch 38 is defined by its side edges 44. The relationship between the side edges 44 that define each notch 38 may be suggested by the desired characteristics of the end of the gripping member 30. For example, side edges 44 that substantially abut provide a slit, while substantially parallel, spaced apart side edges provide a slot-shaped notch. In addition, the side edges 44 may be separated at the edge of the gripping member 30 and converge as the notch 38 extends toward and terminates in the intermediate area 32 in a "V"-shaped notch 38 as shown in FIGS. 1–5. Other notch shapes may be used, including "L"-, "W"-, and "J"-shaped notches, asymmetrical notches, notches having a straight side edge and a shaped side edge, and the like. Slit-shaped notches generally provide an end that can flex radially outwardly to an increased diameter, but limit the ability of the end to take on a reduced diameter. On the other hand, slot- and "V"-shaped notches generally provide flexibility in both inward and outward radial directions. Therefore, an end with such notches could take on both expanded and reduced diameters.

The width of the at least one notch (or cumulative width of a plurality of notches) is selected to allow appropriate adjustment of the diameter of the gripping member during its molding and ejection. If the outside diameter at each end of the gripping member is greater than the minimum outside diameter at an intermediate portion, the width of at least one notch should be sufficient to allow a reduction of the outside diameter to approximately the minimum outside diameter of the intermediate portion. Again, this allows the larger portions of the gripping member to flex to be ejected from the mold, as described below. The notch width can be essentially zero if no significant inward flexing of the gripping member is needed, such as in an member with an essentially constant outside diameter or a consistently increasing or a consistently decreasing outside diameter a varying inside diameter.

We have learned that consumers would like to have small diameter applicators. This improves comfort while inserting the device. However, as the diameter of the applicator decreases, user control correspondingly decreases. In an effort to ensure that the gripping member has sufficient area to grasp during use, especially with relatively small diameter insertion members, the gripping member preferably has a length to diameter ratio of at least about 0.5.

Figure 4:
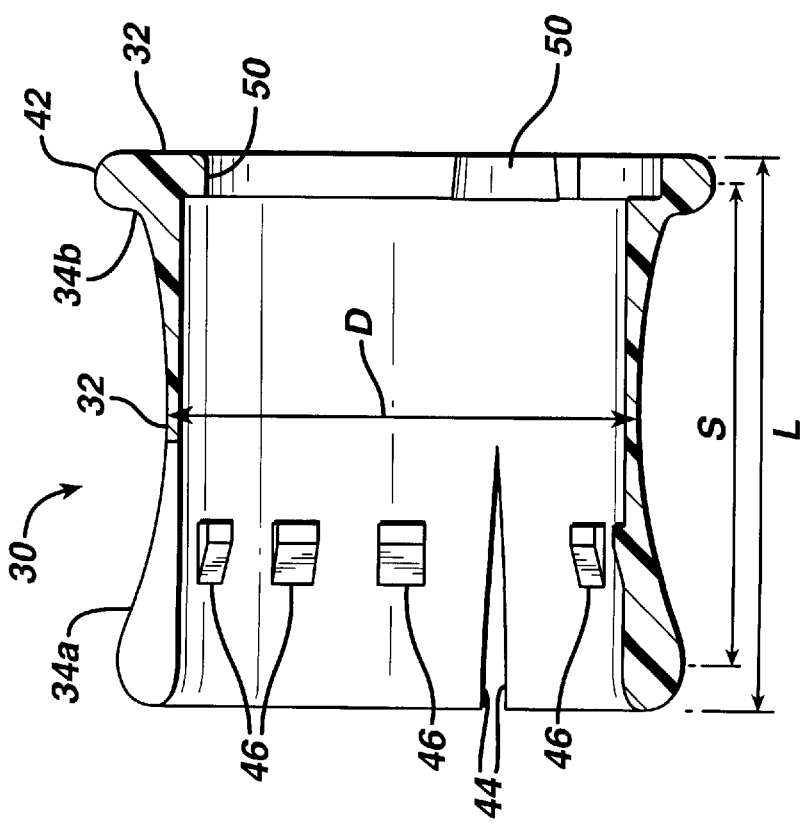
FIG. 4 is a cross-section of the gripping member of FIG. 1 taken along line 2—2.
Figure 6:
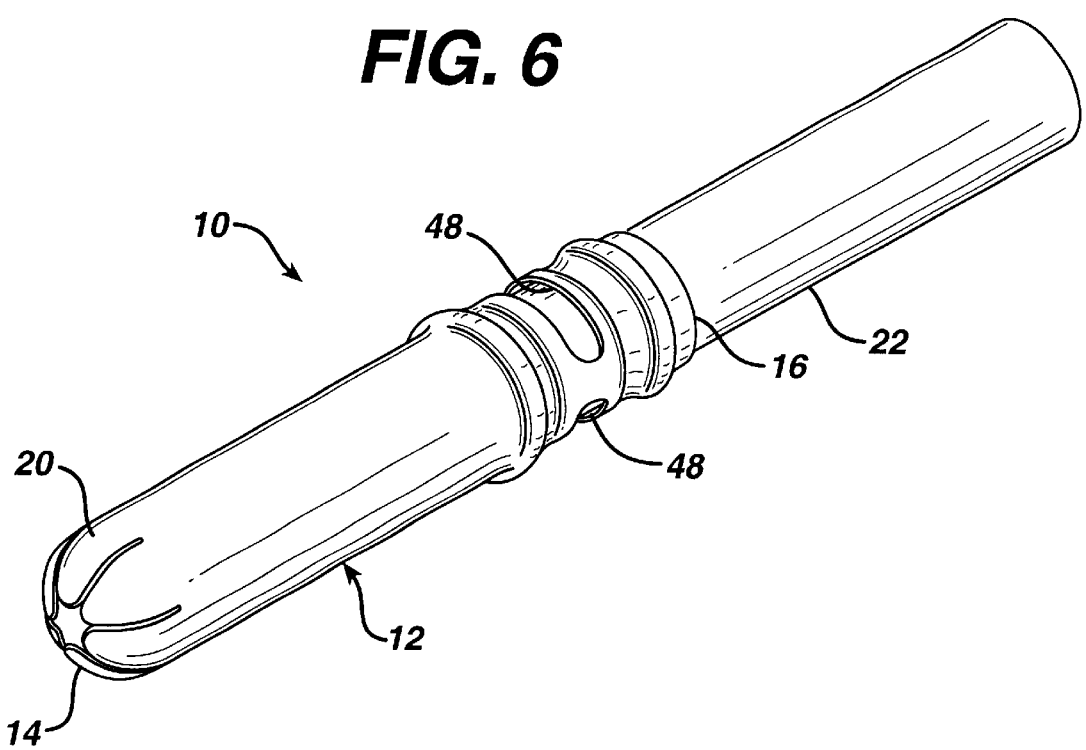
FIG. 6 is a perspective view of the applicator of FIG. 1, shown without the novel gripping member.

A series of optional, inwardly oriented protuberances 46 are also shown in the figures. These improve the fixation of the gripping member to the tubular insertion member. The tubular insertion member may employ a cavity proximate its gripper end 16 end, such as an aperture 48 shown in FIG. 1, which is capable of receiving one or more of the protuberances 46. The cavity may be any generally indented or concave feature that is capable of receiving the protuberances 46, examples including embossed regions and apertures. The cross-sectional view in FIG. 4 illustrates the protuberances 46 residing in a cavity defined by apertures 48 as taught in Hagerty, U.S. Pat. No. 5,709,652, the disclosure of which is herein incorporated by reference. The protuberances may be designed such that they provide additional resistance to separation of the gripping member from the tubular insertion member. For example, the protuberances may be triangulated, or comprise a barb, wherein an apex or barb is capable of pressing into a surface of the tubular insertion member. "Pressing into" may include creating indentations, ruptures, gouges and the like.

Figure 5:
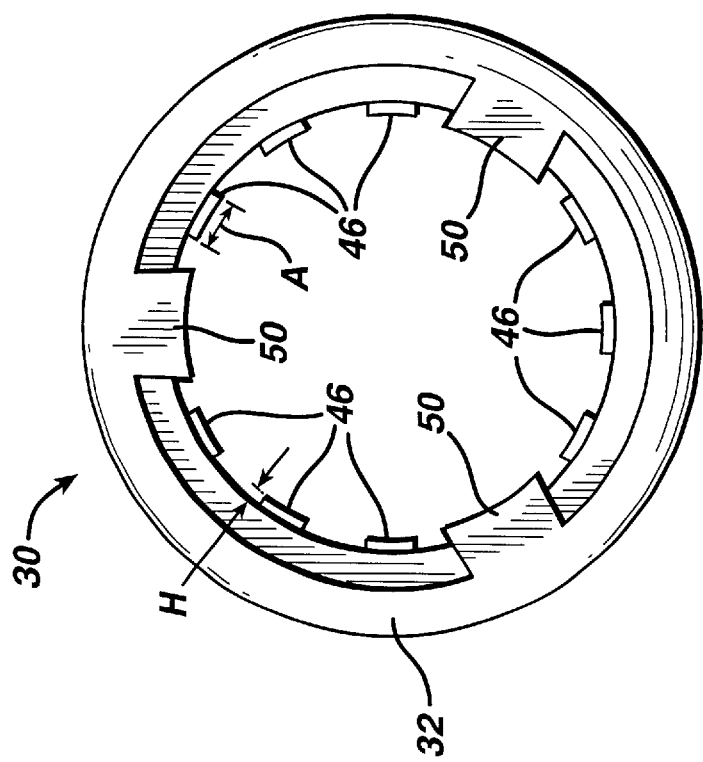
FIG. 5 is an end view of the gripping member shown in FIG. 3, depicting a plurality of the protuberances and stops.

Referring now to FIGS. 4 and 5, preferably the gripping member 30 has from about two to about twelve protuberances, and more preferably from three to nine. The protuberances have a height "H". It may be helpful in some constructions to relate the height of the projection to the thickness of the material forming the tubular insertion member, the manner of attachment of the gripping member, and the relative outside diameter of the tubular member gripper end and the inside diameter of the gripping member. In a press fit attachment, the height "H" is preferably at least about 0.0005 inches (about 0.01 mm), more preferably at least about 0.001 inches (about 0.03 mm). In a mechanical latch attachment, the height "H" may be at least about 0.003 inches (about 0.08 mm), more preferably, at least about 0.005 inches (about 0.1 mm), and most preferably about 0.01 to about 0.02 inches (about 0.3 to about 0.5 mm). The protuberances may have an arc "A" of at least about 0.5°, preferably, in a mechanical latch attachment manner as disclosed in e.g., FIG. 5, an arc of about 3° to about 10°, and most preferably about 5° to about 7°.

The gripping member 30 may optionally have at least one stop 50 extending inwardly from a trailing edge 32, the edge of the gripping member 30 that is the furthest from the insertion end 14 of the tubular insertion member 12, as assembled. The stop 50 is capable of maintaining the gripping member 30 at the gripper end 16 of the tubular insertion member 12. Additionally, FIGS. 4 and 5 illustrate the preferred out-of-phase relationship of the protuberances 46 and the stops 50. This positioning provides the attractive option of using simpler injection molding processes and equipment.

While the figures show a gripping member being affixed to the tubular insertion member overlying a portion of the insertion member gripper end, it may also abut the gripper end of the tubular insertion member. It is likely that an abutting gripping member would not require the protuberances and stops described above.

The gripping member 30 illustrated in FIGS. 2–6 has a curvilinear outer profile, generally "saddle" shaped, wherein the two raised areas 34a and 34b are created by the increasing outer diameters towards the edges of the gripping member. An alternative gripping member outer profile is depicted in FIG. 7, wherein the intermediate area 32 has a flat profile yielding a constant outer diameter along the length, with the two raised areas 34a and 34b being formed by longitudinally separated flanges.

Additional outer profiles are possible, wherein the outer surface has at least one raised area that is capable of providing resistance to movement of a user's manual digit in response to longitudinal forces on the tubular insertion member. All of the figures depict the gripping member having two raised areas separated by an intermediate area; however, a single raised area in conjunction with the other specified design features may be sufficient for the utility of the present invention.

Materials useful for the manufacture of the gripping member include those disclosed above for applicators, in general. Preferred materials are plastics. The gripping member may optionally comprise an additive, either through incorporation into the manufacturing materials, or added to the component through a subsequent processing step. A representative, non-limiting list of additives includes fragrance, odor-neutralizing agents, bacteriostats, bactericides, and moisturizers.

The gripping member outer surface may optionally comprise friction-enhancing means, such as tacky coatings, etched patterns, and the like. Such coatings and/or treatments may be evenly distributed about the outer surface, or they may be restricted to or concentrated in certain, desired portions. The gripping member may be transparent or opaque, and it may be pigmented, as desired. Where a range of differing products is offered to the consumer, the gripping member can be color-coded to indicate a particular product.

The applicator of the present invention can be made by appropriate processes that will be recognized by those of ordinary skill in the art. For example, paper tubular insertion members can be constructed from a single layer of paper material, or from a plurality of laminated layers to provide multiple benefits relating to the various layers. The applicators can be made from sheets of material using several processing including, without limitation: spiral winding as disclosed in Campion et al., U.S. Pat. No. 5,346,468, convolute winding as disclosed in Whitehead, U.S. Pat. No. 4,508,531, and forming a sheet around a mandrel and then sealing an overlapped seam as disclosed in Hinzmann, U.S. Pat. No. 4,755,164.

If the applicator includes a surface layer, as described above, it may be applied using any useful method. Many methods are known for applying the surface layers. A representative, non-limiting list of such methods includes spraying, extruding, slot-coating, brushing, transfer coating, and the like. Additional processing steps may be required to cure the surface treatments to a useable form other than simple air curing, such as applying irradiation or other forms of energy.

Again, the tubular insertion member of the applicator provided by the present invention is preferably substantially closed prior to expulsion of the materials contained therein. One method for substantially closing the insertion end of the applicator is by employing a plurality of inwardly curved petals. The petals will flex and/or hinge to an open position upon expelling materials contained by the applicator. The number of petals generally ranges from about four to about six. An alternative method for substantially closing the insertion end of an applicator is by pleating the insertion end. This method is disclosed in Neilsen et al., U.S. Pat. No. 5,782,793. When an applicator is constructed with more than one layer of material, a single layer may extend into the insertion end in an effort to reduce the force required to expel the contained materials. An example of this is disclosed in Fox et al., U.S. Pat. No. 5,827,214. These collective closures may be of spherical shape, or alternatively tapered shape.

The aperture or cavity 48, if necessary, can be formed in the tubular insertion member 12 by methods recognized by those of ordinary skill in the art. A representative, non-limiting list of methods useful for forming these cavities 48 includes, without limitation, die-cutting, laser cutting, water jet cutting, thermoforming, grinding, and the like.

Plastic applicator members may be manufactured using any useful method, and many methods are known for manufacturing plastic applicators. A representative, non-limiting list of such methods includes injection-molding, blow-molding, extrusion, formation from one or more sheets (as described above for paper), and the like. Generally, the applicator members (for example, the tubular insertion members) can be formed through an injection molding process. This process may be used, because it allows the manufacture to balance some key characteristics of the tubular insertion member. Mold inserts and cores can be machined to form a slightly tapered product. For example, the wall thickness around the gripper end 16 is relatively thick to help to maintain structural stability during the insertion and expulsion steps of use, while the thickness in the insertion end 14 can be minimized to provide flexibility and low expulsion force. Injection molding also enables the manufacture to make uniquely shaped tubular insertion members and expulsion members. As mentioned above, the less sophisticated and/or less expensive methods, such as extrusion and blow molding can also be employed. For example, extruded tubes can be further manipulated to form additional features, such as raised or indented rings or other formations. Extruded plastic tubes provide further orientation of the polymer.

The gripping member can be made from any known methods in the art. Injection molding and blow molding are two such methods useful for making the plastic sleeve of the gripping member 30. Preferably, the gripping member is injection molded.

The present gripping member design provides an easier molding than that disclosed in Binner et al., U.S. Ser. No. 09/602,950, the disclosure of which is hereby incorporated by reference. First, using injection mold methods to mold the parts disclosed in Binner et al, as a single component, a mold having side action (side slides) would usually be used. This side action increases the cycle times and decreases the amount of parts per mold area, both of which increase the costs per part.

Therefore, notches in the present gripping member can relieve stresses induced by ejecting a part with interior enlarged portions from a mold by action along a single mold axis. This can significantly simplify the molding process by eliminating a side-sliding action, an action in a direction substantially perpendicular to the above-mentioned mold axis. This provides a more space-efficient mold structure allowing more parts to be molded per unit of mold surface area. Considering relatively high injection press costs/unit of time, this space-efficient mold structure can greatly reduce molding costs.

One method that can be employed for affixing a separately manufactured gripping member to a tubular insertion member is to press the gripping member onto one end. This method necessitates that the gripping member's smallest outer diameter will be greater than the coincident outer diameter of the tubular insertion member it is combined with. This size differential creates an interference between the element and provides a visual or a tactile cue of applicator insertion depth, and thereafter object positioning within the body cavity. Greater control and handling is also provided with a gripping member having a greater diameter. Applicators known in the art having reduced diameter gripping regions, do so by "necking down" a portion of the tubular insertion member (see for example Huffman, U.S. Pat. No. 4,573,964). As the gripping area is reduced, so is the amount of control by the user. Moreover, an expulsion member used with such an applicator will necessarily become small. Consumers have voiced dislikes associated with small expulsion members.

While the figures show a gripping member being affixed to the tubular insertion member overlying a portion of the insertion member gripper end, it may also abut the gripper end of the tubular insertion member. It is likely that an abutting gripping member would not require the protuberances and stops described above.

The present invention also provides methods for making applicators having retrofitted gripping members, such as those described in relation to FIGS. 1–6. Generally the gripping member may be pressed onto a portion of the tubular insertion member and maintained in its position through the dimensions of each component. Beyond these features, other mechanical features such as suction cups, chemical adhesives, and thermoplastic welding techniques may be used to affix the gripping member or to enhance the fit between the gripping member and the tubular insertion member.

Typical applicators comprise both a tubular insertion member and an expulsion member slideably fitted therein into an opening at the gripper end thereof. The process of assembling the two components, as well as filling the tubular insertion member with an object can vary significantly. Accordingly, the gripping member may be fitted onto a portion of the tubular insertion member prior or after assembly, prior or after filling, and fitted from either end of the tubular insertion member. Useful methods are disclosed in Binner et al., U.S. Ser. No. 09/602,950.

The applicator of the present invention can be used for the delivery of an object into a mammalian body cavity. Such objects may include suppositories, absorbent devices, and the like, and they may be delivered into body cavities including the mouth, nose, vagina, and rectum. These materials may be in the form of solids, creams, foams, gels, and the like.

Preferably, the applicator is used to deliver intravaginal devices, including catamenial devices, such as tampons, intravaginal collection devices, and interlabial pads; birth control devices such as diaphragms or intrauterine devices (IUDs); compositions in the form of suppositories, such as medicaments, moisturizers, vitamins and minerals, spermicides, and odor controlling agents; medical devices and incontinence devices and vaginal supports such as pessaries; and obstructing devices. Obstructing devices include menstrual collection cups and inflatable or expandable blocking devices.

In use, a woman may place insertion end 14 into the body cavity orifice, delivering tampon 18 into the body cavity by pushing on expulsion member 22 until tampon 18 is expelled from cage tubular insertion member 12 and withdrawing applicator 10 from the body, leaving tampon 18 within the body cavity.

Alternately, a user could pull tubular insertion member 12 onto expulsion member 22 while maintaining expulsion member 22 steady relative the user's body. This substantially eliminates friction between the tampon 18 and the user's body.

The specification and embodiments above are presented to aid in the complete and non-limiting understanding of the invention disclosed herein. Since many variations and embodiments of the invention can be made without departing from its spirit and scope, the invention resides in the claims hereinafter appended.

What is claimed is:

1. A gripping member for use on an associated tubular insertion member of an applicator for inserting an object into a body cavity, the gripping member comprising a plastic sleeve having a longitudinal axis; first and second ends; a bore extending from the first end to the second end, the bore having a length, an inner diameter, and a length to inner diameter ratio of at least about 0.5; at least one notch defined by side edges and associated with and disposed pat one of the first and second ends, the notch imparting flexibility to the associated end; an outer surface; and a plurality of raised features disposed on the outer surface of the sleeve, extending away from the longitudinal axis, at least one of the raised features is proximate the first end, at least one of the raised features is proximate the second end, and the raised features proximate the first and second ends are longitudinally separated; wherein the plastic sleeve is arranged and configured to be affixed to the associated tubular insertion member.

2. The gripping member of claim 1 wherein the raised feature proximate the first end is disposed generally about the first end.

3. The gripping member of claim 2 wherein the raised feature proximate the first end comprises a raised ring.

4. The gripping member of claim 3 wherein the raised ring is a continuous ring.

5. The gripping member of claim 3 wherein the raised ring is a discontinuous ring.

6. The gripping member of claim 1 wherein the raised feature proximate the second end is disposed generally about the second end.

7. The gripping member of claim 6 wherein the raised feature proximate the second end comprises a raised ring.

8. The gripping member of claim 7 wherein the raised ring is a continuous ring.

9. The gripping member of claim 7 wherein the raised ring is a discontinuous ring.

10. The gripping member of claim 1 wherein the bore has a substantially circular cross-section.

11. The gripping member of claim 1 comprising a plurality of notches disposed about the associated end.

12. The gripping member of claim 1 wherein the at least one notch is shaped as a slit with its side edges substantially abutting.

13. The gripping member of claim 1 wherein the at least one notch is shaped as a slot with substantially parallel, spaced-apart, side edges.

14. The gripping member of claim 1 wherein the at least one notch has converging side edges.

15. The gripping member of claim 14 wherein the at least one notch is "V"-shaped.

16. The gripping member of claim 1 wherein the raised features proximate the first and second ends have increased outside diameter, and the plastic sleeve has a reduced outside diameter intermediate the first and second ends and longitudinally between the raised features proximate the first and second ends.

17. The gripping member of claim 16 wherein the at least one notch extends to a portion of the plastic sleeve having a minimum outside diameter.

18. A method for forming a gripping member for use on a tubular insertion member of an applicator for inserting an object into a body cavity, the method comprising the steps of:

a) forming a substantially tubular mold cavity between a first mold plate and a second mold plate, the mold cavity having features of increased thickness at a first end and at a second end and at least one notch-forming insert in the mold cavity disposed at one of the first and second ends;

b) injecting molten plastic material into the mold cavity;

c) cooling the plastic material in the mold cavity to form the gripping member having a first end and a second end corresponding to the first and second ends of the mold cavity and at least one flex-enhancing notch corresponding to the at least one notch-forming insert in the mold cavity; and d) opening the mold and ejecting the gripping member whereby the at least one notch allows the end associated therewith to flex sufficiently to permit separating the mold plates and stripping the gripping member.

19. The method of claim 18 wherein the opening of the mold and the ejection of the gripping member occurs through action of the mold plates and an ejection element along a single mold axis.

* * * * *